United States Patent [19]

Brossi et al.

[11] 4,388,463
[45] Jun. 14, 1983

[54] 6-KETO-MORPHINAN ANALGESICS

[75] Inventors: Arnold Brossi; Helmut Schmidhammer, both of Bethesda; Arthur E. Jacobson, Potomac; Fu-Lian Hsu, Rockville, all of Md.

[73] Assignee: The United States of America as represented by Secretary of the Department of Health and Human Services, Washington, D.C.

[21] Appl. No.: 284,088

[22] Filed: Jul. 16, 1981

[51] Int. Cl.$^3$ ................ C07D 221/28; A61K 31/485
[52] U.S. Cl. .................................... 546/74; 424/260; 546/45
[58] Field of Search .......................... 546/74; 424/260

[56] References Cited

U.S. PATENT DOCUMENTS 3,914,233 10/1975 Mohacsi et al. .................. 546/74

FOREIGN PATENT DOCUMENTS 20863 9/1965 Japan ................................ 546/74
6905 4/1966 Japan ................................ 546/74

OTHER PUBLICATIONS

Schmidhammer, et al., Heterocycles, vol. 17, pp. 391–394, (1981).
Jacobson, et al., Problems in Drug Dependence, 1981, National Institute on Drug Abuse Research, Monograph, vol. 41, pp. 86–92, (1982).
Zakkrzewski (I), Farmacja Polska, vol. 27, No. 9, pp. 695–698, (1971).
Brossi, et al., Chemical Abstracts, vol. 95, 187481j, (1981).
Reden et al., J. Med. Chem., vol. 22, No. 3, pp. 256–259, (1979).

Chemical Abstracts, Chemical Subject Index (E-O), vol. 76, Jun. 30, 1972, morphinan, morphin-6-one.
Hsu et al., Heterocycles, 1979, 13 (Spec. Issue), 259–61.
Hsu et al., Helv. Chim. Acta 1980, 63(7), 2042–5.
Rozwadowska et al., Can. J. Chem. 1980, 58(17), 1855–9.
Zakrzewski, Chemical Abstracts, vol. 76, 50006w (1972).

Primary Examiner—Nicholas S. Rizzo
Assistant Examiner—Diana G. Rivers
Attorney, Agent, or Firm—John S. Roberts, Jr.

[57] ABSTRACT

This patent application describes the preparation and properties of novel and highly potent morphinan analgesics. The compounds include narcotic agnoists as well as narcotic antagonists and are represented by the following formula:

$R_1$=OCH$_3$, OCOCH$_3$, H $R_2$=CH$_3$, CH$_2$—CH=CH$_2$,

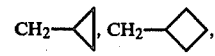

CH$_2$CH$_2$C$_6$H$_5$

12 Claims, No Drawings

6-KETO-MORPHINAN ANALGESICS

This patent application describes the preparation and properties of novel and highly potent morphinan analgesics. The compounds include narcotic agonists as well as narcotic antagonists and are represented by the following formula:

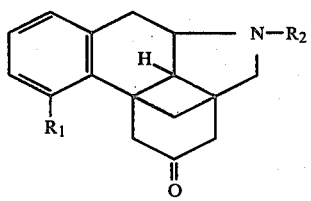

$R_1$ = OCH$_3$, OCOCH$_3$, H
$R_2$ = CH$_3$, CH$_2$—CH=CH$_2$,

CH$_2$CH$_2$C$_6$H$_5$

Relative to the stereoisomerism of the above compounds, the optical isomers having the natural configuration present in morphine (— —) are preferred, although the unnatural isomers (+ +) can be obtained synthetically as by total synthesis.

It has long been known that morphinans having a phenolic hydroxy group at C-3 were valuable therapeutic agents, and one compound has been denoted "Levorphanol" (see Table). It was taught that etherification in this series of compounds is accompanied by a loss of analgesic activity and that putting the hydroxy group into the 4-position would be disadvantageous. However, in the present invention it has been found that where the C-ring contains at C-6 a carbonyl function, etherification of 4-hydroxy-6-keto-N-methylmorphinans affords highly potent analgesics when etherified, contrary to the findings made in the nonketonic 3-hydroxy series.

The antinociceptive potency of the several optically active N-methylmorphinan-6-ones prepared from natural morphinan were determed and the results were in the following order of antinociceptive potency: 4-methoxy-N-methylmorphinan-6-one~3,4-dimethoxy-N-methylmorphinan-6-one>4-acetoxy-N-methylmorphinan-6-one>4-hydroxy-N-methylmorphinan-6-one. The 4-hydroxy compounds were slightly less potent than morphine, and the 4-methoxy and 3,4-dimethoxy compounds were found to have three times the potency of morphine. The 4-acetyl group where present may hydrolyze quickly in vivo, thus showing antinociceptive potency comparable to its 4-hydroxyl relative. In the 6-keto series the dimethoxy compound is considerably more potent than its hydroxy relative.

TABLE

Structures of Opioids and Opioid Antagonists Chemically Related to Morphine

| Nonproprietary Name | Chemical Radicals and Positions | | | Other Changes# |
|---|---|---|---|---|
| | 3* | 6* | 17* | |
| Morphine | —OH | —OH | —CH$_3$ | — |
| Heroin | —OCOCH$_3$ | —OCOCH$_3$ | —CH$_3$ | — |
| Hydromorphone | —OH | =O | —CH$_3$ | (1) |
| Oxymorphone | —OH | =O | —CH$_3$ | (1),(2) |
| Levorphanol | —OH | —H | —CH$_3$ | (1),(2) |

*The numbers 3, 6, and 17 refer to positions in the morphine molecule, as shown above.
Other changes in the morphine molecule are:
(1) Single instead of double bond between C7 and C8
(2) OH added to C14
(3) No oxygen between C4 and C5

Prior Art Statement

Jacobson et al, *Helvetica Chimica Acta*, July, 1981.

U.S. Pat. No. 2,732,375 Gates—Dihydrothebainone which possesses the 4-hydroxy-6-keto structure and also there may be 3,4-dimethoxy-N-methyl-6-dehydroisomorphinan.

U.S. Pat. No. B 3,810,899 Mohacsi et al—4-Hydroxy morphinan derivatives; apparently lacks the 6-keto.

U.S. Pat. No. 3,914,232 Mohacsi et al—Shows 4-acyloxy morphinan derivatives; similar to U.S. Pat. No. 3,914,234 Mohacsi et al.

U.S. Pat. No. 4,230,712 Kotick et al—Touches on cis-trans isomers of morphinan-6-one compounds.

British No. 1,330,581 Merck & Co. —At page 1 shows the 4-hydroxy-6-keto-morphinan alkaloid and the 4,5-oxide bridge.

The specific compounds of this invention are:
(−)-4-hydroxy-6-keto-N-methylmorphinan
(−)-4-methoxy-6-keto-N-methylmorphinan
(−)-6-ketomorphinan
(±)-2,4-dihydroxy-6-keto-N-formylmorphinan
(±)-4-hydroxy-6-keto-N-formylmorphinan
(−)-4-methoxy-6-keto-N-methylmorhinan
(−)-4-methoxy-6-keto-N-allylmorphinan
(−)-4-acetoxy-6-keto-N-methylmorphinan
(−)-4-methoxy-6-keto-N-cyclopropylmethylmorphinan
(−)-4-methoxy-6-keto-N-cyclobutylmethylmorphinan
(−)-4-methoxy-6-keto-N-phenethylmorphinan
(−)-6-keto-N-methylmorphinan
(−)-6-keto-N-allylmorphinan
(−)-6-keto-N-phenethylmorphinan
(±)-4-hydroxy-6-keto-N-methylmorphinan
(±)-4-methoxy-6-keto-N-methylmorphinan
(±)-4-methoxy-6-keto-N-cyclopropylmethylmorphinan
(±)-4-methoxy-6-keto-N-allylmorphinan Included with the above compounds as acid addition salts are certain pharmaceutically acceptable soluble salts such as hydrochlorides, sulfates, phosphates, tartrates, succinates, etc.

The compounds with the natural configuration, can be obtained from 3-deoxydihydromorphinone, being a convenient starting material. The latter is easily available from natural morphine by the procedure of Reden et al, *J. Med. Chem.* 22, 256 (1979). Conversion of 3-deoxydihydromorphinones prepared from (±)-4-hydroxy-2-(1-phenyltetrazolyloxy)-N- formyl-morphinan-6-one by conventional methods [Rozwadowska et al, *Can. J. Chem.*, 58, 1855 (1980)] affords either the nor compound or directly the 6-ketomorphinans, depending on the reduction method used. A preferred method is to reduce the trichloroethoxycarbamate with Zn in methanol in the presence of ammoniumchloride, affording in excellent yield the nor ketone. Reduction of (±)-4-hydroxy-2-(1-phenyltetrazolyloxy)-N-formyl-morphinan-6-one by the same procedure affords directly the 6-ketomorphinan, which after acetylation, gives the highly active analgesic agonist. Introduction of the 4-methoxy function can also be accomplished by two routes. Methylation of the 4-hydroxy ketone with diazomethane in either, or other appropriate solvents, affords the narcotic agonist (4-methoxy-N-methylmorphinan-6-one). The latter can preferably be obtained by treatment with an alkylating agent, such as dimethylsulfate in DMF or another appropriate solvent, to afford the enol ether (5,6-didehydro-4,6-dimethoxy-N-formylmorphinan). The latter can be hydrolyzed with acid, such as 20% methanolic hydrochloric acid at elevated temperatures, to afford the nor ketone (4-methoxymorphinan-6-one) by simultaneous cleavage of the enolether function in ring C and the N-formyl protecting group. 4-Methoxymorphinan-6-one, which itself has no analgesic properties, is an extremely useful intermediate for preparing 4-methoxy- N-methylmorphinan-6-one and N-allyl-4-methoxymorphinan6-one. The compound 4-methoxy-N-methylmorphinan-6-one can be made by reductive N-methylation of 4-methoxymorphinan-6-one in the presence of aqueous formaldehye in hydrogen atmosphere over metal catalysts such as Raney-Ni, Pd, Pd/C or Pt. The compound N-allyl-4-methoxymorphinan-6-one can be obtained by alkylating the amine (4-methoxymorphinan-6-one) with an alkylating agent such as allylbromide to afford N-allyl-4-methoxymorphinan-6-one. This alkylation follows standard methods, a preferred route if to alkylate the free base in DMF or other solvent in the presence of an acid scavenger such as potassium carbonate. The analgesics here are basic materials which can easily be converted into salts by treatment with hydrogen halides in solvents such as acetone, ethylacetate or ether. Preferred acids are hydrochloric acid or hydrobromic acids, or organic acids such as tartaric acid, succinic acid, etc.

Norketone [(−)-4-acetoxy-6-keto-N-methylmorphinan] of the natural series constitutes a valuable intermediate for preparing N-substitution noted for antagonist activities. A preferred route to enter into such classes of compounds consists in acylating the nor ketone with commercially available chlorides such as cyclopropylcarbonylchloride and cyclobutylcarbonylchloride to afford the amides (N-cyclopropylcarbonyl-4-methoxymorphinan-6-one and N-cyclobutylcarbonyl-4-methoxymorphinan-6-one). This acylation is preferably executed in solvents such as DMF or THF in the presence of an acid scavenger, such as potassium carbonate or pyridine. Reduction of these two amides above affords a mixture of carbinols, which, after oxidation, afford the wanted morphinans. A preferred way for oxidizing the mixtures of epimeric carbinols is the Oppenauer oxidation (Reden et al, ante), but chemical oxidizing agents, such as pyridinium chromate or manganese dioxide may be used. Morphinans are crystalline bases which can be used as such, preferably in combinations, or converted into salts such as hydrochlorides, hydrobromides, phosphates, tartrates, etc., useful for injectable preparations.

This application covers also 6-ketomorphinans. These compounds can be obtained by the elimination of the phenolic oxygen function in the ketone. This can be accomplished by elimination of a phosphate ester with lithium in refluxing ammonia or the elimination of the phenolic oxygen function via its phenyltetrazolyl ether derivatives, such as N-methyl-4-(1-phenyl-1H-5-tetrazolyloxy)morphinan-6-one. The latter can easily be obtained by reacting the phenolic species with commercially available chlorophenyltetrazole in an inert solvent such as acetone. The tetrazolyl ether derivatives can then be reduced catalytically, preferentially in acetic acid solution in the presence of sodium acetate at temperatures between 20°–50° C. in the presence of catalysts such as Pd/C or Pt/C to afford in high yield the deoxycompounds such as N-methylmorphinan-6-one. Under these experimental conditions the carbonyl group is not affected. N-methylmorphinan-6-one may be converted adding antagonist side chains.

Total synthesis of compounds covered in this application starts from the 2,4-dihydroxy-6-ketomorphinan of the racemic series. Optical resolution to obtain compounds of the natural series, or unnatural series if desired, can be attempted at the tetrahydroisoquinoline stage by chemical resolution. Chemical resolving agents used repeatedly in the TIQ series of compounds are tartranilic acis, tartaric acids, camphersulfonic acids, etc.

The elimination of the 2-hydroxy group can again be perfected by deoxygenation of the tetrazolylether, formed besides its isomeric ether by treatment with chlorophenyltetrazole in DMF in the presence of potassium carbonate. Catalytic reduction of the tetrazolylether affords (±)-racemate which can be methylated with dimethylsulfate to afford the enol ether. Acid hydrolysis cleaves the N-formyl protecting group and unmasks the ketone to give an intermediate, which can now be methylated, N-allylated, or cyclopropylmethylated. Chemical resolution of the racemic morphinans can also be carried out at the morphinan stage by chemical resolution. It is, however, preferred to do that at the TIQ stage where the possibility exists that the unwanted optical isomer can be converted in a useful racemate.

EXAMPLE 1

5,6-Didehydro-4,6-dimethoxy-N-formylmorphinan

A solution of 1 g (3.89 mmol) N-formyl-4-hydroxymorphinan-6-one in 10 ml dry DMF was dropped during 5 min. to a mixture of 210 mg (8.75 mmol) sodium hydride and 1.63 g (8175 mmol) methyl p-toluenesulfonate in 10 ml dry DMF. This mixture was stirred at room temperature for 15 h and then poured on 40 g of ice and extracted with a total amount of 125 ml ether. The organic layer was washed with brine, dried and the solvent removed in vacuo. The semicrystalline residue was crystallized with ether/μ-hexane to give 750 mg (68%) pure 5,6-didehydro-4,6-dimethoxy-N-formylmorphinan, m.p. 169°–172°, $[\alpha]_D^{26}$ −215.5° (c 0.97, CHCl$_3$).

EXAMPLE 2

4-Methoxymorphinan-6-one 600 mg (1.91 mmol) 5,6-didehydro-4,6-dimethoxy-N-formylmorphinan were dissolved in 13.5 ml methanol and 1.5 ml 37% hydrochloric acid were added. This mixture was heated at reflux for 17 h, then the solvent was removed in vacuo, the oily residue dissolved in water and rendered alkaline with 30% NH$_4$OH. After extraction with CHCl$_3$, the organic layer was washed with brine, dried and evaporated to give an oil, which was crystallized with ether to yield 450 mg (81%) 4-methoxymorphinan-6-one. 1 H$_2$O m.p. 136°–138°, $[\alpha]_D^{26}$ −75.7° (c=0.88, CHCl$_3$).

EXAMPLE 3

4-Methoxy-N-methylmorphinan-6-one

4-Methoxymorphinan-6-one was reductively alkylated with Pt/C/H$_2$/CH$_2$Ox to yield 4-methoxy-N-methylmorphinan-6-one. The material was identical with an authentic sample.

EXAMPLE 4

N-Allyl-4-methoxymorphinan-6-one

A mixture of 700 mg (2.44 mmol) 4-methoxymorphinan-6-one.1H$_2$O, 900 mg (6.51 mmol) anhydrous K$_2$CO$_3$ and 310 mg (2.56 mmol) allyl bromide in 20 ml dry DMF was stirred at 80° C. for 30 min. Then the mixture was cooled to room temperature, filtered, and the filtrate evaporated in vacuo. The resulting oil was partitioned between water and ether, the organic layer washed with brine, dried and evaporated to give an oil which was crystallized with u-hexanes. To 700 mg (93%) N-allyl-4-methoxymorphinan-6-one, m.p. 84°–86°, $[\alpha]_D^{26}$ −114.6° (c 0.79, CHCl$_3$), were obtained.

EXAMPLE 5

N-Cyclopropylcarbonyl-4-methoxymorphinan-6-one

To a mixture of 1.5 g (5.18 mmol) 4-methoxymorphinen-6-one.1 H$_2$O, 1.3 g (9.41 mmol) anhydrous K$_2$CO$_3$ and 10 ml dry DMF were added dropwise a solution of 0.29 ml (5.31 mmol) cyclopropanecarboxylic acid chloride in 5 ml dry DMF during 10 min. at room temperature. This mixture was stirred at room temperature for 1 h, then poured on 50 ml ice water and extracted with ether. The organic layer was extracted with 2 N HCl, water and brine, dried and evaporated to give an oil, which was crystallized with ether/n-hexane. To 1.5 g (85%) N-cyclopropylcarbonyl-4-methoxymorphinan-6-one, m.p. 144°–147°, $[\alpha]_D^{26}$ −210.0° (c 1.04, CHCl$_3$), were obtained.

EXAMPLE 6

N-Cyclopropylmethyl-4-methoxymorphinan-6-one.HCl

A solution of 580 mg (1.71 mmol) N-cyclopropylcarbonyl-4-methoxymorphinan-6-one in 25 ml dry ether was dropped during 10 min. at room temperature to a slurry of 400 mg (10.54 mmol) LAH in 25 ml dry ether. The resulting mixture was refluxed for 4 h. Then saturated Na$_2$SO$_4$ solution was added slowly until all LAH was destroyed. The organic layer was separated and the aqueous layer was extracted 2x with ether. The combined organic layers were extracted with 25 ml 1 N HCl, the aqueous layer was basified with 2 N NaOH and extracted with ether. The ether extract was washed with brine, dried and evaporated to give 550 mg of a semicrystalline residue. A solutio of this residue and 3.06 g (16.79 mmol) benzophenone in 15 ml dry toluene was dropped at room temperature during 10 min. to a slurry of 565 mg (5.03 mmol) KOtBu in 30 ml dry toluene under argon. This mixture was heated to 85°–90° C. (bath temperature) for 1 hr, then cooled to room temperature. The mixture was extracted with 2×30 ml 2 N HCl. The aqueous layer was washed with ether, rendered alkaline with conc. NaOH and extracted with ether. The ethanol solution was washed with brine, dried and evaporated to give 540 mg of an oil, which was dissolved in ether and treated with ether/HCl. The resulting precipitate was recrystallized with ethanol/ether to yield 480 mg (77%) N-cyclopropylmethyl-4-methoxymorphinan-6-one.HCl, m.p. 284°–286° (dec), $[\alpha]_D^{26}$ −57.6° (c 1.1, CHCl$_3$).

EXAMPLE 7

N-Cyclobutylcarbonyl-4-methoxymorphinan-6-one

To a mixture of 2 g (7.37 mmol) 4-methoxymorphinan-6-one (H$_2$O was removed azeotropic) and 3 g (21.71 mmol) K$_2$CO$_3$ in 20 ml dry DMF was dropped at room temperature during 15 min. a solution of 900 mg (7.59 mmol) cyclobutanecarboxylic acid chloride. This mixture was stirred at room temperature for 1 h, then poured on 200 ml ice water and extracted with ether. The organic layer was extracted with 2 N HCl and brine, dried and evaporated to give an oil, which was crystallized with benzene/u/hexane to yield 2.5 g (96%) N-cyclobutylcarbonyl-4-methoxymorphinan-6-one, m.p. 125°–126°, $[\alpha]_D^{26}$ −204.5° (c 0.76, CHCl$_3$).

EXAMPLE 8

N-Cyclobutylmethyl-4-methoxymorphinan-6-one.HCl

A solution of 1.2 g (3.40 mmol) N-cyclobutylcarbonyl-4-methoxymorphinan-6-one in 30 ml dry ether was dropped during 15 min. at room temperature to a slurry of 400 mg (10.54 mmol) LAH in 30 ml dry ether. The resulting mixture was refluxed for 3 h. Then saturated Na$_2$SO$_4$ solution was added slowly until all LAH was destroyed. The organic layer was separated and the aqueous layer was extracted 2×with ether. The combined organic layers were washed with brine, dried and evaporated to give 1 g of a colorless oil. A solution of this oil and 5.3 g (29.08 umol) benzophenone in 20 ml dry toluene was dropped at room temperature during 10 min. to a slurry of 986 mg (8.78 umol) KOtBu in 50 ml dry toluene under argon. This mixture was heated to 85°–90° C. (bath temperature) for 70 min., then cooled to room temperature. The mixture was extracted with 2×60 ml 2 N HCl. The aqueous layer was washed with ether, rendered alkaline with conc. NaOH and extracted with ether. The etheral solution was washed with brine, dried and evaporated to give 1 g of an oil, which was dissolved in ether and treated with ether/HCl. The resulting precipitate was recrystallized with ethanol/ether to yield 770 mg (60%) N-cyclobutylmethyl-4-methoxymorphinan-6-one.HCl, m.p. 248°–251° (dec.), $[\alpha]_D^{26}$ −49.3° (c 0.97, CHCl$_3$).

EXAMPLE 9

N-Methyl-4-(1-phenyl-1H-5-tetrazolyloxy)morphinan-6-one

A mixture of 1.57 g (5.79 mmol) 4-hydroxy-N-methylmorphinan-6-one, 1.57 g (11.36 mmol) dry K$_2$CO$_3$ and 1.15 g (6.37 mml) 5-chloro-1-phenyl-1H-tetrazole din 30 ml dry DMF was stirred under argon for 24 h at room temperature. Then the reaction mixture was filtered, washed with CHCl$_3$ and the filtrate was evaporated in vacuo (70° bath temperature). The oily residue was dissolved in CHCl$_3$ and extracted with 2×20 ml 5% tartaric acid. The aqueous layer was rendered alkaline with conc. NaOH and extracted with CHcl$_3$. The organic layer was washed with brine, dried and evaporated to give 2.2 g of an oil, which was crystallized with EtOAc/Et$_2$O to yield 2.05 g (85%) of N-methyl-4-(1-phenyl-1H-5-tetrazolyloxy) morphinen-6-one, m.p. 172°–174°, $[\alpha]_D^{26}$ −37.4° (c 1.35, $CHCl_3$).

EXAMPLE 10

N-Methylmorphinan-6-one

To a solution of 350 mg (0.84 mmol) of the tetrazolylether in 20 ml glacial acetic acid were added 650 mg of 10% Pd/C and this mixture was hydrogenated at 50 psi for 16 h at room temperature. The catalyst was filtered off and the filtrate was evaporated in vacuo. The oily residue was dissolved in $CHCl_3$ and extracted with 2×10 ml 5% tartaric acid. The aqueous layer was washed with $Et_2O$, rendered alkaline with conc. NaOH and extracted with $CHCl_3$. The organic layer was washed with brine, dried and evaporated to give 200 mg of a crystalline solid, which was recrystallized with isopropyl ether to yield 165 mg (77%) N-methylmorphinan-6-one, m.p. 164°–166°, $[\alpha]_D^{26}$ −137.8° (c 0.92, $CHCl_3$).

EXAMPLE 11—Racemate Series

A. (±)-4-Hydroxy-2-(1-phenyltetrazolyloxy)-N formyl-morphinan-6-one

A mixture of 2,4-dihydroxy-N-formylmorphinan-6-one (3.6 g, 12 mmol), 5-chloro-1-phenyltetrazole (2.3 g, 12.7 mmol) and anhydrous $K_2CO_3$ (8.4 g, 60.8 mmol) in 150 ml DMF was stirred at 80+5° C. for 16 hrs uner $N_2$. The $K_2CO_3$ was filtered off and washed with 10 ml DMF. The combined filtrates were evaporated under vacuum to afford a dark brown residue which was taken up in 200 ml 2 N NaOH and the aqueous solution washed with ether (2×100 ml). The basic solution was the acidified with conc. HCl and extracted with $CHCl_3$:i-PrOH=3:2. The combined organic extracts were washed with brine, dried over sodium sulfate and evaporated to give 6.3 g of a gum. The crude product was chromatographed over silica gel and eluted with $CHCl_3$/MeOH=40:1 to give 1.3 g of pure ketone which after crystallization from DMF-EtOAc had a m.p. of 254°–256°.

B. (±)-4-Hydroxy-N-formylmorphinan-6-one

The tetrazolyl ether (in A above) (1.1 g, 2.47 mmol) was dissolved in 60 ml of hot AcOH. After cooling to room temperature 2.2 g of 10% Pd/C catalyst was added and the reaction mixture hydrogenated at 45 psi at 60°–65° for 48 hrs. The catalyst was filtered off and washed with hot AcOH. The combined filtrates were evaporated under vacuum to afford an oil which was dissolved in $CHCl_3$ and washed with 10% $Na_2CO_3$, brine, and dried over sodium sulfate. Evaporation of the solvent left 1.19 g of a foam, which was chromatographed on silica gel and eluted with $CHCl_3$/MeOH=40:1, then $CHCl_3$/MeOH=20:1 to give (±)-2 of m.p. 260°–262° C. after crystallization from methanol. Further fraction contains the corresponding alcohol.

C. (±)-4-Methoxymorphinan-6-one

This compound was prepared from the phenol in B above in analogy to the cases described in the natural series. In this case the phenol in B above was methylated with methyl-p-toluenesulfonate to afford after hydrolysis with aqueous methanolic HCl the norketone, which after crystallization from methanol-ether had a m.p. of 52°–53° C. This compound has been found identical, except optical behavior, to material prepared in the natural series. Reductive N-methylation of this compound gave (±)-4-methoxy-N-methylmorphinan-6-one, which showed half of the antinociceptive activity measured for the natural enantiomer.

EXAMPLE 12

(−)-4-Acetoxy-6-keto-N-methylmorphinan

A mixture of (−)-4-hydroxy-N-methylmorphinan-6-one (500 mg, 1.84 mmol), acetic anhydride (5 ml), and pyridine (10 ml) was stirred at room temperature overnight. Acetic anhydride and pyridine were evaporated under vacuum and the residue was taken into toluene and evaporated again. The crude product was taken into $CHCl_3$ and washed with $H_2O$, dried and evaporated to give a foam which was recrystallized from $iPr_2O$-hexane to afford (301 mg, 65%). An analytical sample was recrystallized from $iPr_2$: mp 96°–97°; $[\alpha]_D^{26}$ −46.7° (c 1.126, $CHCl_3$).

EXAMPLE 13

(−)-4-Methoxy-6-keto-N-methylmorphinan

Method A. A solution of (−)-4-hydroxy-N-methylmorphinan-B 6-one (500 mg, 1.84 mmol) in 20 ml of $CHCl_3$ was treated with $CH_2N_2$ ethereal solution and stirred at room temperature overnight. Excess $CH_2N_2$ was decomposed with AcOH and the low boiling point solvents were evaporated. The resulting solution was basified with 10% NaOH and extracted with $CHCl_3$. The combined $CHCl_3$ solution was washed with brine, dried and evaporated to give a crude solid which was passed through alumina column ($CHCl_3$) to yield (−)-4-methoxy-N-methylmorphinan-6-one (340 mg, 65%). An analytical sample was recrystallized from benzene-petroleum ether: mp 145°–147°; $[\alpha]_D^{26}$ −96.5° (c 1.02, $CHCl_3$).

The hydrochloride salt was prepared and recrystallized from EtOH-ether to afford (−)-4-methoxy-N-methylmorphinan-6-one hydrochloride mp 268°–271° (dec); $[\alpha]_D^{26}$ −33.8° (c 1.01, $CH_3OH$).

Method B. To a solution of (−)-4-hydroxy-N-methylmorphinan-6-one (500 mg, 1.84 mmol) in 6 ml of DMF, sodium methoxide (109 mg, 2.02 mml) and phenyltrimethylammonium chloride (347 mg, 2.02 mmol) were added. This mixture was stirred at 80° (bath temperature) under argon for 2 h. The mixture was cooled to room temperature and then poured into 50 ml of ice water and extracted with ether. The ether layer was washed with brine, dried, and evaporated in vacuum at 90° to give 540 mg solid which was recrystallized from benzene-petroleum ether to afford (−)-4-methoxy-N-methylmorphinan-6-one (390 mg, 74%).

We claim:
1. A compound according to the following formula and pharmaceutically acceptable acid addition salts thereof:

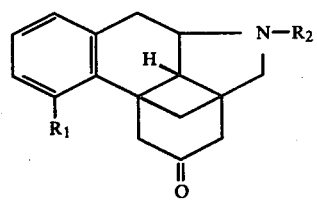

where $R_1$=$OCH_3$, $OCOCH_3$, or H; $R_2$=$CH_3$, $CH_2$—CH=$CH_2$, $CH_2-$, or $C_2H_2CH_6CH_5$.

2. The compound according to claim 1 wherein the stereochemistry is the same as in natural morphine and is designated (−)-.

3. The compound according to claim 1 wherein the stereochemistry is similar to that from synthetic oxymorphine and is designated (±)-.

4. The compound according to claim 1 wherein $R_1$ is $OCH_3$ and $R_2$ is $CH_3$.

5. The compound according to claim 1 wherein $R_1$ is $OCH_3$ and $R_2$ is $CH_2-CH=CH_2$.

6. The compound according to claim 1 wherein $R_1$ is $OCOCH_3$ and $R_2$ is $CH_3$.

7. The compound according to claim 1 wherein $R_1$ is $OCH_3$ and $R_2$ is

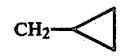

8. The compound according to claim 1 wherein $R_1$ is $OCH_3$ and $R_2$ is

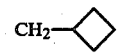

9. The compound according to claim 1 wherein $R_1$ is $OCH_3$ and $R_2$ is $C_6H_5CH_2CH_3$.

10. The compound according to claim 1 wherein the $R_1$ position is unsubstituted and $R_2$ is methyl.

11. The compound according to claim 1 wherein the $R_1$ position is unsubstituted and $R_2$ is $CH_2-CH=CH_2$.

12. (−)-6-Ketomorphinan.

* * * * *